United States Patent [19]

Riihimaki et al.

[11] 4,323,782

[45] Apr. 6, 1982

[54] ABSORPTION RESOLUTION TESTING DEVICE

[75] Inventors: Esko Riihimaki, Espoo; Seppo Savikurki, Helsinki, both of Finland

[73] Assignee: Hospital Physics Oy, Finland

[21] Appl. No.: 125,980

[22] Filed: Feb. 29, 1980

[30] Foreign Application Priority Data

Mar. 8, 1979 [FI] Finland .................................. 790798

[51] Int. Cl.[3] ............................ G02B 5/00; A61B 6/00

[52] U.S. Cl. ...................................................... 250/252

[58] Field of Search ..................... 250/252, 445 T, 320

[56] References Cited

U.S. PATENT DOCUMENTS 3,348,319 10/1967 Harrison ............................. 250/320
4,124,799 11/1978 Schittenhelm ...................... 250/252
4,126,789 11/1978 Vogl et al. .......................... 250/252
4,233,507 11/1980 Volz .................................... 250/252

FOREIGN PATENT DOCUMENTS 402070 1/1974 U.S.S.R. .............................. 250/252

*Primary Examiner*—Bruce C. Anderson
*Attorney, Agent, or Firm*—McGlew and Tuttle

[57] ABSTRACT

An absorption resolution testing device for use in connection with X-ray imaging devices, for example, computer tomography devices includes a vessel containing a liquid which has X-ray radiation absorption values approximately equal to living tissue and a plurality of smaller vessels disposed within the vessel and the liquid. A second liquid is disposed within the smaller vessels and has absorption values which are different from the absorption values of the first liquid in the vessel.

10 Claims, 2 Drawing Figures

ABSORPTION RESOLUTION TESTING DEVICE

BACKGROUND OF THE INVENTION

The present invention relates to an absorption resolution testing device for X-ray apparatus designed to be used, for example, in connection with X-ray computer tomography systems. Testing devices of this kind are used for determination of the imaging property of the tomographic equipment. This kind of devices can be used for determination of the spatial resolution and absorption resolution of the computer tomography devices. Because absorption resolution is the important characteristic property of the computer tomography devices it is important that this property can also be tested.

Prior art are known devices which are designed for measurement of the absorption resolution which consist, for example, of of polycarbonate plastic with holes and plastic plugs in these holes which have different absorption values. There devices can be utilized for cheking the numerical absorption value given by a computer tomography device if the absorption values are printed out with a line printer or otherwise processed with the computer in numerical form. The draw back of a device of this type is that if a comparison of two devices with respect to the imaging property is desired either a computer output or computer processing is required. From the pictures generated by these devices, it is not readily apparent to the naked eye whether the devices which produced images have differences in quality.

SUMMARY OF THE INVENTION

The aim of the present invention is to avoid the drawbacks of the prior art devices noted above and produce a device whereby, from the pictures produced from the device, one can visually determine whether two imaging devices have a difference in their absorption resolution property.

Thus, it is an object of the invention to provide an absorption resolution testing device for use in connection with X-ray imaging devices, for example, computer tomography devices, comprising a vessel, a first liquid within the vessel which has X-ray radiation absorption values approximately equal to living tissue, and a plurality of smaller vessels disposed within the vessel and the first liquid, and a second liquid inside the smaller vessels having absorption values which are different from the absorption values of the first liquid inside the vessel. In accordance with preferred embodiments of the invention, the first liquid is distilled water and the second liquid is sugar dissolved in water in an amount between 0.1 and 2.0% by weight.

The device according to the present invention has several advantages as compared with other previously known devices. The most important advantage is the fact that the imaging property of the computer tomography device can be observed from day to day just by simply taking a picture of the testing device. Furthermore devices of different make can easily be compared with each other just by making a picture under normal conditions from testing device.

It is a further object of the invention to provide an absorption resolution testing device which is simple in design, rugged in construction and economical to manufacture.

For an understanding of the principles of the invention, reference is made to the following description of a typical embodiment thereof as illustrated in the accompanying drawing.

DESCRIPTION OF PREFERRED EMBODIMENT

Figure 1:
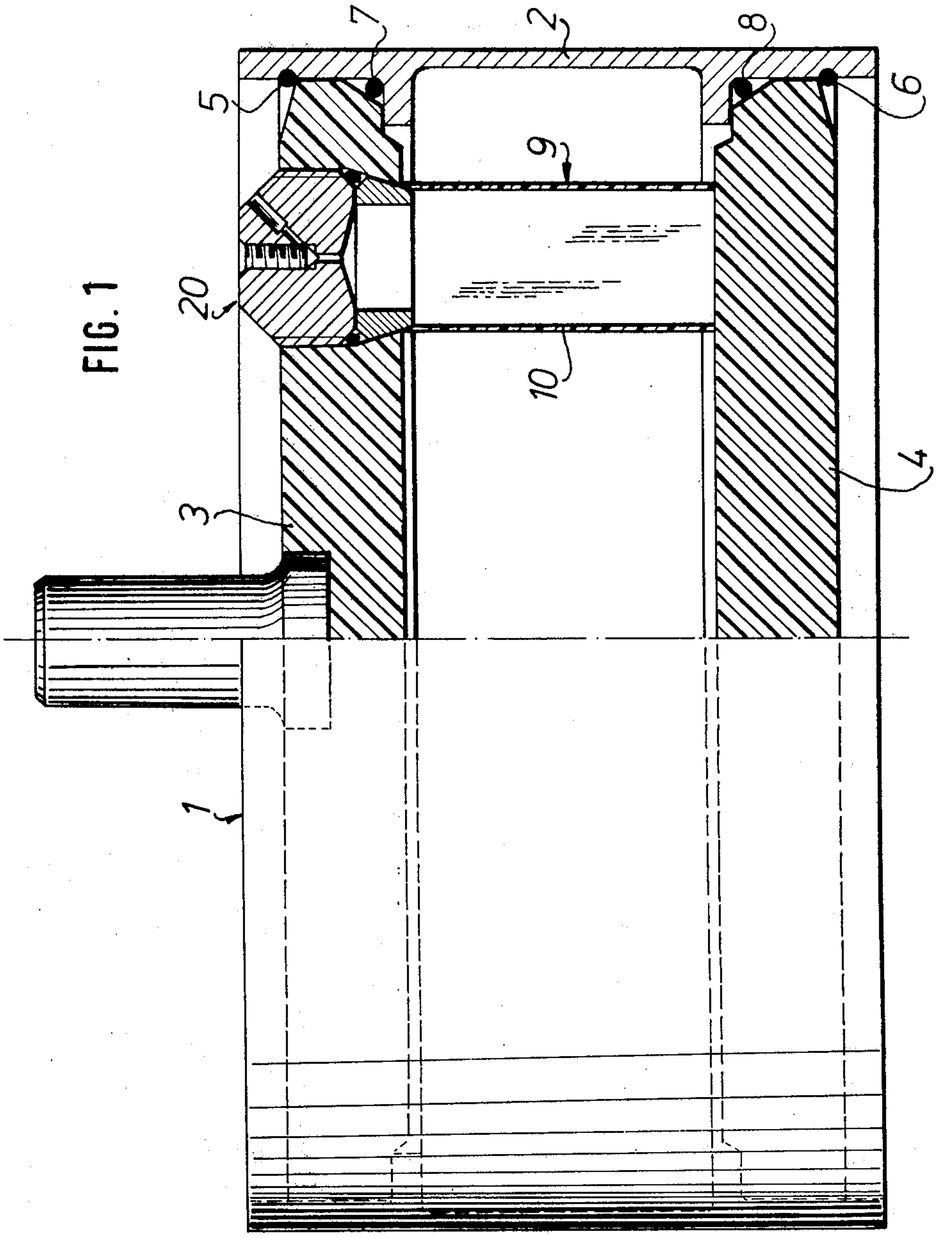
FIG. 1 is a side elevation, partly in section, of a device made in accordance with the invention.

A testing device according to present invention has been presented in FIG. 1. This device can be used e.g. for the testing of the head computed tomography devices. The device consists of vessel 1 which has a form of a cylinder 2 and two caps 3 and 4. The cylinder 2 has been manufactured from aluminum with a diameter, for example, of 20 cm. The wall thickness of the cylinder is preferrably about three milimeters so that the absorption in the cylinder corresponds to the absorption in the bones of the skull. Caps 3 and 4 are made, for example, out of acrylic plastic. Caps 3 and 4 have been fastened to cylinder 2 with locking rings 5 and 6. Caps 3 and 4 and cylinder 2 have been made waterproof by O-rings 7 and 8 which are disposed between the periphery of the caps 3, 4 and inside surface of the cylinder 2. Within vessel, 1 there are smaller vessels 9.

Ten of the smaller vessels 9, for example, may be positioned at the same radius inside the large vessel. Smaller vessels 9 are separated from the larger by a membrane 10. Membrane 10 has been formed in a tubular fashion in such a way that it extends from cap 3 to cap 4. Material and thickness of membrane 10 has been chosen in such a way that membrane 10 will not be visible, that is, is transparent in the process of taking a picture by a computer tomography device. Smaller vessels 9 have been fastened to lower cap 4 in waterproof fashion. In the upper cap 3, at each position of the smaller vessels 9, there is a locking device 20 which can be fastened tight.

Figure 2:
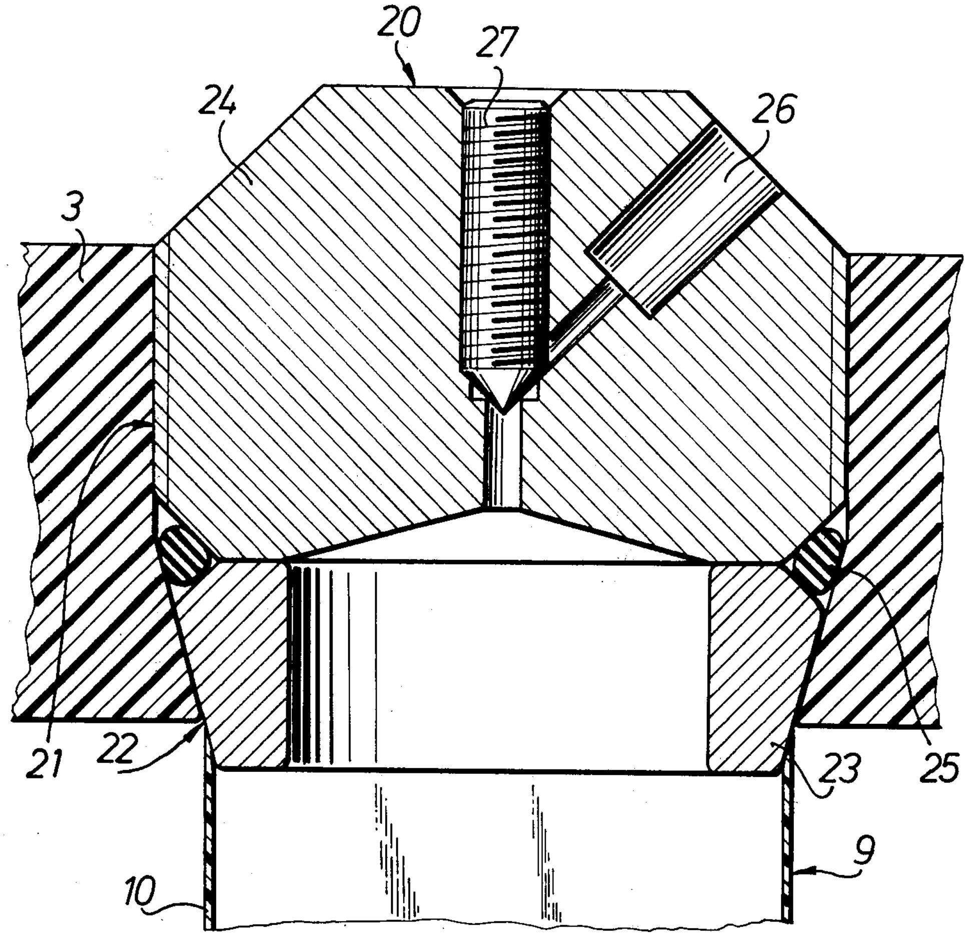
FIG. 2 is a cross-sectional view of a portion of the inventive device.

In FIG. 2 is an illustration of cross cut view of a locking device 20. As shown in FIG. 2, the cap 3 is provided with a generally cylindrical bore extending therethrough in alignment with the position of each smaller vessel 9. The lower part of the bore, as illustrated, conically tapers so that one end of the bore has a smaller cross-section than the other end of the bore. The lower part of the bore is formed in a conical shape 22 and contains a cylindrical insert 23 having a conical outer surface and a cylindrical inner surface. The function of the cylindrical insert 23 is to tighten the joint between membrane 10 and cap 3. The 23 has been pressed into its position by a plug 24. In between plug 24 and insert 23 there is O-ring 25 in addition. In order to readily facilitate an exchange of liquid in vessel 9 without opening the plug 24, a passage 26 is provided in plug 24 for fluid communication with vessel 9 which can be filled, for example, with an injection syringe. Passage 26 can be opened and closed by screw 27.

In medical investigations, the computed tomographs are used for measuring living tissues the density of which are very close to the density of water. Therefore, vessel 1 can be filled, for example, with distilled water and the smaller vessels 9 can be filed with some organic substance which is water soluble. Sugar is used for this purpose. Suitable solute concentrations range between 0.1 and 2.0 percent by weight.

When an image is taken with a computer tomograph from the device according to present invention, a picture will be produced. In this picture one can see in the cross cut view of the testing device a circle and inside this usually a few smaller circles. The smaller circles are pictures of the solutions in the smaller vessels 9 which have different absorption properties. Another picture can be made by placing the device into another computer tomograph. The pictures can be compared with each other to find out whether equal number of smaller vessels can be seen. If this is the case, the absorption resolutions of both devices are equally good within the precision that can be obtained with the concentration differences in the liquids in the smaller chambers. The sensitivity of the testing devices can be changed in practice in any desired way by changing concentration differences in the smaller vessels with respect to the large vessel. The device according to present invention is suitable also for the follow up of an imaging quality of an imaging device even daily. By taking a picture of the testing device and comparing the picture with the one taken earlier it is immediately evident whether the absorption resolution has changed or remained the same. The invention has been described above by referring to only one preferred embodiment. It is naturally clear that the explained embodiment is only an example and the invention is not to be limited to the said example. On the contrary many changes in the construction of an apparatus according to the invention are possible without departing from the basic inventive idea expressed in the following patent claims.

While a specific embodiment of the invention has been shown and described in detail to illustrate the application of the principles of the invention, it will be understood that the invention may be embodied otherwise without departing from such principles.

I claim:

1. An absorption resolution testing device for testing the spatial resolution and the absorption resolution of computer tomography devices, comprising a larger vessel, a first liquid within said larger vessel, and a plurality of smaller vessels disposed within said larger vessel and said first liquid, a second liquid inside the smaller vessels having absorption values which are different from the absorption values of the first liquid inside said larger vessel, wherein the first liquid is distilled water and the second liquid comprises sugar dissolved in water in an amount between 0.1 and 2.0 percent by weight, and wherein said smaller vessels are of a wall thickness and materials such that they are transparent in computer tomography pictures.

2. The testing device according to claim 1 wherein the second liquid inside each of the smaller vessels has a different concentration.

3. A testing device according to claim 1, wherein said larger vessel is a cylinder and each of the smaller vessels is a circular tube and extends from one end of said larger vessel to the other end thereof.

4. The testing device according to claim 3 further comprising locking means on each of said smaller vessels provided at least on one end having a passage through which the second liquid inside each smaller vessel can be exchanged.

5. The testing device according to claim 1 further comprising locking means on each of said smaller vessels provided at least on one end having a passage through which the second liquid inside each smaller vessel can be exchanged.

6. The testing device according to claim 4 or 1 wherein said larger vessel is made of a material having approximately the same X-ray absorption value as bone.

7. The testing device according to claim 3, wherein the second liquid inside each of the smaller vessels has a different concentration.

8. The testing device according to claim 4, wherein the second liquid inside each of the smaller vessels has a different concentration.

9. The testing device according to claim 6, wherein the second liquid inside each of the smaller vessels has a different concentration.

10. The testing device according to claim 6, wherein said larger vessel is composed of aluminum having a thickness of approximately 3 mm.

* * * * *